US012599552B2

(12) United States Patent
Lee et al.

(10) Patent No.: US 12,599,552 B2
(45) Date of Patent: Apr. 14, 2026

(54) **COSMETIC COMPOSITION CONTAINING EXTRACT OF *CYPERUS ROTUNDUS* FOR ANTI-INFLAMMATION, SKIN SOOTHING, IRRITATION RELIEF, AND SKIN BARRIER ENHANCEMENT**

(71) Applicant: J2KBIO CO., LTD., Cheongju-si (KR)

(72) Inventors: Jae Soeb Lee, Cheongju-si (KR); Jun Tae Bae, Cheongju-si (KR); Jun Hwan Jang, Cheongju-si (KR); Ah Reum Jung, Cheongju-si (KR); Na Ri Kim, Cheongju-si (KR); Ji Yeon Lee, Cheongju-si (KR); So Hyun Mun, Cheongju-si (KR)

(73) Assignee: J2KBIO CO., LTD., Cheongju-si (KR)

( * ) Notice: Subject to any disclaimer, the term of this patent is extended or adjusted under 35 U.S.C. 154(b) by 278 days.

(21) Appl. No.: 18/463,921

(22) Filed: Sep. 8, 2023

(65) Prior Publication Data

US 2024/0189219 A1    Jun. 13, 2024

Related U.S. Application Data

(63) Continuation of application No. PCT/KR2023/009358, filed on Jul. 4, 2023.

(30) Foreign Application Priority Data

Dec. 8, 2022    (KR) ........................ 10-2022-0170937

(51) Int. Cl.
| | |
|---|---|
| *A61K 36/00* | (2006.01) |
| *A61K 8/9789* | (2017.01) |
| *A61Q 19/00* | (2006.01) |

(52) U.S. Cl.
CPC ............ *A61K 8/9789* (2017.08); *A61Q 19/00* (2013.01); *A61K 2800/75* (2013.01)

(58) Field of Classification Search
CPC ................................................... A61Q 19/00
See application file for complete search history.

(56) References Cited

U.S. PATENT DOCUMENTS 11,110,117 B2    9/2021  Lee et al.

FOREIGN PATENT DOCUMENTS

| | | | |
|---|---|---|---|
| JP | 62-234006 A | | 10/1987 |
| JP | 2003137726 A | * | 5/2003 |
| KR | 10-2013-0062112 A | | 6/2013 |
| KR | 2013062112 A | * | 6/2013 |
| KR | 2018079850 A | * | 7/2018 |
| KR | 10-2222661 B1 | | 3/2021 |

OTHER PUBLICATIONS

Khan et al., Sesquiterpene derivatives isolated from *Cyperus rotundus* L. inhibit inflammatory signaling mediated by NF-kB. Natural Product Sciences (2011), vol. 17, No. 3, pp. 250-255. (Year: 2011).*
Korean Office Action of No. 10-2022-0170937 dated Jan. 10, 2023.
Communication issued Jul. 8, 2025 in Japanese Application No. 2023-557021.

* cited by examiner

*Primary Examiner* — Qiuwen Mi
(74) *Attorney, Agent, or Firm* — Sughrue Mion, PLLC

(57) ABSTRACT

The present disclosure relates to a cosmetic composition containing an extract of *Cyperus rotundus* extracted using warm microbubbles. The extract inhibits nitric oxide (NO) production and exhibits excellent anti-inflammatory efficacy by inhibiting the expression of interleukin 6 (IL-6), cyclooxygenase-2 (COX-2), interleukin-1β (IL-1β), and tumor necrosis factor-α (TNF-α), which are inflammatory expression factors. In addition, the extract enhances the expression of aquaporin-3 (AQP-3), hyaluronan synthase 2 (HAS-2), claudin-1 (CLDN-1), cadherin 1 (CDH1), filaggrin (FLG), and involucrin (IVL), which are genes related to the skin barrier and moisturizing. Thus, when using the extract for cosmetic products, excellent effects can be exhibited in skin soothing, moisturizing, enhancement of the skin barrier, relief of irritation such as erythema, relief of pruritus, and the like, so the extract can be usefully applied to multi-care products that improve skin conditions.

8 Claims, 3 Drawing Sheets
Specification includes a Sequence Listing.

COSMETIC COMPOSITION CONTAINING EXTRACT OF *CYPERUS ROTUNDUS* FOR ANTI-INFLAMMATION, SKIN SOOTHING, IRRITATION RELIEF, AND SKIN BARRIER ENHANCEMENT

CROSS-REFERENCE TO RELATED APPLICATIONS

This application is a bypass continuation of International Application No. PCT/KR2023/009358, filed Jul. 4, 2023, which is based on and claims priority to Korean Patent Application No. 10-2022-0170937, filed Dec. 8, 2022, the disclosures of which are incorporated herein by reference in their entireties.

INCORPORATION BY REFERENCE OF SEQUENCE LISTING

The content of the electronically submitted sequence listing, file name: Q291267_sequence listing as filed.xml; size: 22,260 bytes; and date of creation: Nov. 30, 2025, filed herewith, is incorporated herein by reference in its entirety.

TECHNICAL FIELD

The present disclosure relates to a cosmetic composition for anti-inflammation, skin soothing, irritation relief, and skin barrier enhancement, which contains an extract of *Cyperus rotundus* prepared by a microbubble extraction method.

BACKGROUND ART

*Cyperus rotundus*, a perennial herb belonging to the Cyperaceae family, grows naturally in southern Korea and Jeju Island, and the ingredients thereof including pinene, camphene, 1,8-cineol, limonene, and the like, which contain essential oil components, are known for pain relief and antibacterial action. However, extraction by a static extraction method using an existing solvent may be subject to certain constraints when utilizing active ingredients of *Cyperus rotundus*.

Microbubbles are used in various fields by applying sterilization and cleaning functions using physicochemical properties, such as gas dissolution effect, self-compression effect, charging effect, and the like, oxidation-reduction action of micro-sized bubbles, and a large amount of energy generated when bubbles disappear.

Recently, products and services using the functionality of microbubbles have been developed, thereby gradually increasing the application fields, and are widely applied to all industries related to food, medicine, agriculture, fisheries, dyeing, and the like. Microbubbles are also used for the extraction of natural ingredients, as in Korean Patent No. 10-2222661.

Accordingly, while researching various physiological activities of *Cyperus rotundus*, the inventors of the present disclosure confirmed that extracts of *Cyperus rotundus* extracted using microbubbles had better efficacies of anti-inflammation, skin soothing, irritation relief, and skin barrier enhancement than existing extracts extracted using static methods and thus were available as a novel cosmetic composition, thereby completing the present disclosure.

2

DOCUMENT OF RELATED ART

Patent Document (Patent Document 1) Korean Patent Application Publication No. 2013-0062112 (Title of Invention: Skin external composition for preventing and treating inflammatory diseases containing extract of *Cyperus rotundus* as active ingredient, Applicant: Korean Oriental Medicine Industry Promotion Institute, Publication Date: Jun. 12, 2013)

(Patent Document 2) Korean Patent No. 10-2222661 (Title of Invention: Preparation method of extract of raw material for natural cosmetic product using warm microbubbles and cosmetic composition containing same, Applicant: J2K Bio Co., Ltd., Registration Date: Aug. 24, 2020)

(Patent Document 3) US Patent Registration No. 11110117 (Title of Invention: Skin preparation composition for external use containing complex hyaluronic acid, Applicant: J2K Bio Co., Ltd., Registration Date: Sep. 7, 2021)

DISCLOSURE

Technical Problem

An objective of the present disclosure is to provide a cosmetic composition for anti-inflammation, skin soothing, irritation relief, and skin barrier enhancement, which contains an extract of *Cyperus rotundus* prepared by a microbubble extraction method.

Technical Solution

The present disclosure relates to an anti-inflammatory and skin-soothing cosmetic composition containing an extract of *Cyperus rotundus* extracted using warm microbubbles.

The extract may contain α-cyperone in an amount in a range of 50000 to 60000 ppm.

Preferably, the extract is characterized by inhibiting nitric oxide (NO) production. In addition, the extract has an efficacy of inhibiting the expression of a gene selected from the group consisting of interleukin 6 (IL-6), cyclooxygenase-2 (COX-2), interleukin-1β (IL-1β), and tumor necrosis factor-α (TNF-α), which are inflammatory expression factors.

The extract may have an efficacy of enhancing the skin barrier. In addition, the extract may have a moisturizing efficacy by preventing transepidermal water loss and increasing skin moisture content. Preferably, the extract is characterized by enhancing the expression of a gene selected from the group consisting of aquaporin-3 (AQP-3), hyaluronan synthase 2 (HAS-2), claudin-1 (CLDN-1), cadherin 1 (CDH1), filaggrin (FLG), and involucrin (IVL).

In addition, the extract may have an efficacy of relieving skin irritation. Preferably, the extract relieves skin erythema or improves pruritus, thereby relieving skin irritation and soothing skin.

The extraction using the warm microbubbles may be performed using a microbubble generator with a pore size in a range of 5 to 50 μm and a discharge rate (or liquid flow rate) in a range of 1.0 to 1.2 Ton/hr. In addition, the extraction may be performed using an organic solvent at a temperature in a range of 40° C. to 60° C. for 3 to 5 hours. In this case, the extraction efficiency is the best when generating the microbubbles under the following generation conditions: a gas flow rate in a range of 3 to 4 L/min and a pressure in a range of 3 to 4 bar.

The organic solvent may be an alcohol having 1 to 4 carbon atoms, or an aqueous solution of the alcohol having 1 to 4 carbon atoms. The alcohol having 1 to 4 carbon atoms may be methanol, ethanol, propanol, isopropanol, butanol, and isobutanol. In addition, the aqueous solution of the alcohol having 1 to 4 carbon atoms may be an aqueous solution of the alcohol having 1 to 4 carbon atoms at a volume concentration in a range of 40% to 60% (v/v).

The organic solvent may be used at a volume of 1 to 40 times (1 to 40 L for 1 kg) for the weight of the used *Cyperus rotundus*.

The extract of the present disclosure may contain a fraction thereof. As used herein, the term "fraction" refers to a product obtained by performing fractionation to separate a specific component or a specific component group from a mixture containing various components.

The fractionation method for obtaining the fraction of the present disclosure is not particularly limited and may be performed according to a method commonly used in the art. Examples of the fractionation method may include a solvent fractionation method performed by treating various solvents, an ultrafiltration fractionation method performed by passing through an ultrafiltration membrane having a predetermined molecular weight cut-off value, a chromatographic fractionation method performed by various chromatography (made for separation depending on size, charge, hydrophobicity, or affinity), and combinations thereof. The type of fractionation solvent used to obtain the fraction of the present disclosure is not particularly limited, and any solvent known in the art may be used. Non-limiting examples of the fractionation solvent of the present disclosure may include a polar solvent, such as water, an alcohol having 1 to 4 carbon atoms, and the like, and a non-polar solvent, such as hexane, ethyl acetate, chloroform, dichloromethane, and the like. These examples may be used alone or in combination of one or more.

The chromatography may be selected from among silica gel column chromatography, LH-20 column chromatography, ion exchange resin chromatography, medium-pressure liquid chromatography, thin-layer chromatography (TLC), silica gel vacuum liquid chromatography, and high-performance liquid chromatography.

In addition, the present disclosure provides a pharmaceutical composition for anti-inflammation, skin soothing, irritation relief, and skin barrier enhancement, which contains the extract of *Cyperus rotundus* extracted using the warm microbubbles. The extract of *Cyperus rotundus* may be added to the pharmaceutical composition of the present disclosure in an amount in a range of 0.001% to 100% by weight.

The pharmaceutical composition may be formulated and used in the form of oral formulations, such as powders, granules, tablets, capsules, suspensions, emulsions, syrups, aerosols, and the like, external preparations, suppositories, and sterile injection solutions, according to respective common methods. Examples of carriers, excipients, and diluents that may be included in the pharmaceutical composition may include lactose, dextrose, sucrose, sorbitol, mannitol, xylitol, erythritol, maltitol, starch, gum acacia, alginate, gelatin, calcium phosphate, calcium silicate, cellulose, methylcellulose, microcrystalline cellulose, polyvinylpyrrolidone, water, methylhydroxybenzoate, and propylhydroxybenzoate, talc, magnesium stearate, and mineral oil. In the case of being formulated, excipients or diluents, such as commonly used fillers, extenders, binders, wetting agents, disintegrating agents, and surfactants, may be used for preparation. Solid preparations for oral administration may include tablets, pills, powders, granules, capsules, and the like. In addition, these solid preparations are prepared by mixing the extract of *Cyperus rotundus* of the present disclosure with at least one excipient, for example, starch, calcium carbonate, sucrose or lactose, gelatin, and the like. Furthermore, not only excipients but also lubricants, such as magnesium stearate and talc, are used. While examples of liquid preparations for oral administration include suspensions, liquid preparations for internal use, emulsions, syrups, and the like, not only diluents, such as water and liquid paraffin but also various excipients, such as wetting agents, sweetening agents, fragrances, preservatives, and the like, may be included. Examples of formulations for parenteral administration include sterile aqueous solutions, non-aqueous solvents, suspensions, emulsions, freeze-dried formulations, and suppositories. As for non-aqueous solvents and suspensions, propylene glycol, polyethylene glycol, vegetable oils such as olive oil, injectable esters such as ethyl oleate, and the like may be used. As for suppository bases, witepsol, macrogol, tween 61, cacao fat, laurin fat, glycerogelatin, and the like may be used.

A dosage of the pharmaceutical composition of the present disclosure may vary depending on the age, sex, and weight of a subject to be treated, a specific disease or pathological condition to be treated, the severity of the disease or pathological condition, administration route, and the decision of a prescriber. Dosage determinations based on these factors fall within the level of those skilled in the art. The pharmaceutical composition is typically administered at a dosage in a range of 0.01 mg/kg/day to approximately 2000 mg/kg/day and preferably administered at a dosage in a range of 1 mg/kg/day to 500 mg/kg/day. The pharmaceutical composition may be administered once or multiple times a day. The dosage is not intended to limit the scope of the present disclosure in any way.

Mammals, such as rats, livestock, and humans, may be administered the pharmaceutical composition of the present disclosure through various routes. While all administration methods are predictable, oral administration, rectal administration, intravenous administration, intramuscular injection, subcutaneous injection, intrauterine injection, or intracerebroventricular injection may be performed. The extract of *Cyperus rotundus* of the present disclosure has almost no toxicity and side effects, and thus is safely usable even when taken for a long period for preventive purposes.

In addition, the present disclosure provides health functional food for anti-inflammation, skin soothing, irritation relief, and skin barrier enhancement, which contains the extract of *Cyperus rotundus* extracted using the warm microbubbles and a sitologically acceptable food supplement additive. The extract of *Cyperus rotundus* may be added to the health functional food of the present disclosure in an amount in a range of 0.001% to 100% by weight. The health functional food of the present disclosure may be provided in the form of tablets, capsules, pills, or liquids. Examples of food to which the extract of the present disclosure is addible may include a variety of drinks, meat, sausages, bread, candy, snacks, noodles, ice cream, dairy products, soups, ionic beverages, soft drinks, alcoholic beverages, chewing gum, tea, vitamin complexes, and the like.

The cosmetic composition containing the extract of *Cyperus rotundus* extracted using the warm microbubbles may be prepared in any formulations conventionally prepared in the art, which may be provided in the form selected from an essence, a lotion, an emulsion, a face mask, a hand cream, a foot cream, a lip balm, a lipstick, an eye shadow, an eyeliner, an eyebrow pencil, a blush, a highlighter, a common toner lotion, facial water, a cream, a serum, a beauty soap, a softening toner lotion, a medicated toner lotion, a body cleanser, a facial wash, a cleansing lotion, a gel, a cleansing oil, a cleansing cream, a shampoo, a conditioner, a hair treatment, a hair lotion, a cleansing tissue, and cleansing water.

More specifically, in the case of formulating the cosmetic composition of the present disclosure into a paste, a cream, or a gel, an animal fiber, a vegetable fiber, a wax, paraffin, a starch, tragacanth, a cellulose derivative, polyethylene glycol, silicone, bentonite, silica, talc, zinc oxide, or the like may be used as a carrier component. In the case of formulating the cosmetic composition of the present disclosure into a powder or a spray, lactose, talc, silica, aluminum hydroxide, calcium silicate, or polyamide powder may be used as a carrier component. In particular, when being formulated into a spray, propellants, such as chlorofluoro-hydrocarbon, propane/butane, or dimethyl ether may be additionally included. In the case of formulating the cosmetic composition of the present disclosure into a solution or an emulsion, a solvent, a solvation agent, or an emulsifier may be used as a carrier component, which, for example, includes water, ethanol, isopropanol, ethyl carbonate, ethyl acetate, benzyl alcohol, benzyl benzoate, propylene glycol, 1,3-butyl glycol oil, glycerol aliphatic ester, polyethylene glycol, or fatty acid ester of sorbitan. In the case of formulating the cosmetic composition of the present disclosure into a suspension, liquid diluents, such as water, ethanol, or propylene glycol, suspension agents, such as ethoxylated isostearyl alcohol, polyoxyethylene sorbitol ester, and poly-oxyethylene sorbitan ester, microcrystalline cellulose, aluminum metahydroxide, bentonite, agar or tragacanth may be used as a carrier component. In the case of formulating the cosmetic composition of the present disclosure into a sur-factant-containing cleanser, aliphatic alcohol sulfate, ali-phatic alcohol ether sulfate, sulfosuccinic acid monoester, isethionate, an imidazolinium derivative, methyl taurate, sarcosinate, fatty amide ether sulfate, acid alkylamido-betaine, aliphatic alcohol, fatty acid glyceride, fatty acid diethanolamide, vegetable oil, a lanolin derivative, ethoxy-lated glycerol fatty acid ester, or the like may be used as a carrier component. The cosmetic composition of the present disclosure may further contain excipients including fluores-cent substances, fungicides, hydrotropes, moisturizers, fra-grances, fragrance carriers, proteins, solubilizers, sugar derivatives, sunscreens, vitamins, plant extracts, and the like. The amount of the components added may be selected within a range that does not impair the inherent effect of the cosmetic composition, depending on the formulations or purposes of use. The amount of the components added may be, for example, in a range of 0.1% to 10% by weight and preferably in the range of 0.1% to 6% by weight, with respect to the total weight of the composition, but is not limited thereto.

Advantageous Effects

The present disclosure relates to a cosmetic composition containing an extract of *Cyperus rotundus* extracted using warm microbubbles. The extract inhibits nitric oxide (NO) production and exhibits excellent anti-inflammatory efficacy by inhibiting the expression of interleukin 6 (IL-6), cyclooxygenase-2 (COX-2), interleukin-1β (IL-1β), and tumor necrosis factor-α (TNF-α), which are inflammatory expression factors. In addition, the extract enhances the expression of aquaporin-3 (AQP-3), hyaluronan synthase 2 (HAS-2), claudin-1 (CLDN-1), cadherin 1 (CDH1), filag-grin (FLG), and involucrin (IVL), which are genes related to the skin barrier and moisturizing. Thus, when using the extract for cosmetic products, excellent effects can be exhib-ited in skin soothing, moisturizing, enhancement of the skin barrier, relief of irritation such as erythema, relief of pruri-tus, and the like, so the extract can be usefully applied to multi-care products that improve skin conditions.

DESCRIPTION OF DRAWINGS

FIG. 1 is a graph showing the result that a cream con-taining an extract of *Cyperus rotundus* extracted using warm microbubbles of the present disclosure has the effect of relieving pruritus;

FIG. 2 is a graph showing the result that a cream con-taining an extract of *Cyperus rotundus* extracted using warm microbubbles of the present disclosure has the effect of preventing transepidermal water loss.

MODE FOR INVENTION

Figure 3:
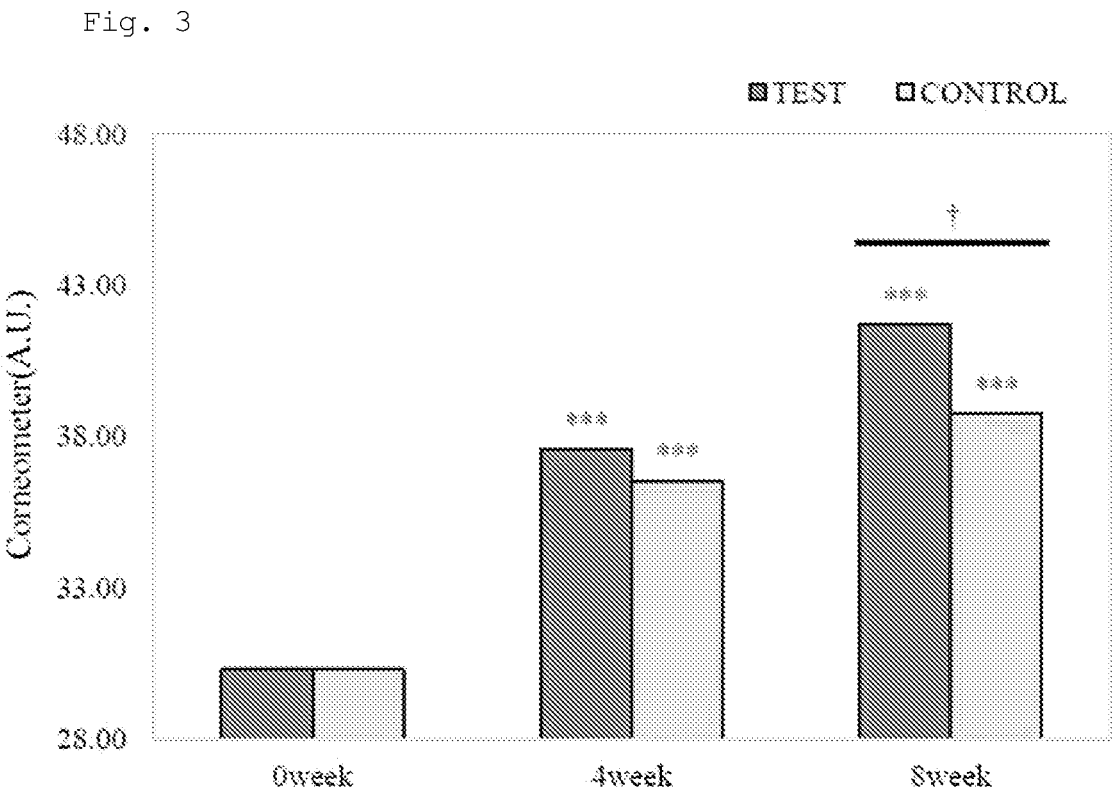
FIG. 3 is a graph showing the result that a cream con-taining an extract of *Cyperus rotundus* extracted using warm microbubbles of the present disclosure has the effect of increasing skin moisture content.

Hereinafter, preferred embodiments of the present disclo-sure will be described in detail. However, the present disclosure is not limited to the embodiments described herein and may be embodied in other forms. Rather, the embodiments are provided to sufficiently convey the spirit of the disclosure to those skilled in the art, so that the disclosure herein will be thorough and complete.

Examples 1 to 3. Preparation of Extract of *Cyperus rotundus* Using Microbubbles

*Cyperus rotundus* (nutgrass flatsedge, *Cyperus rotundus* root) was purchased from Samhong medicinal herb market (South Korea). 100 g of *Cyperus rotundus* was injected into a microbubble generator (manufacturer: O2Bubble) with a pore size in a range of 5 to 50 μm and a discharge rate (liquid flow rate) in a range of 1.0 to 1.2 Ton/hr along with 2000 g (a weight ratio of 1:20) of 50 (v/v) % ethanol aqueous solution as a solvent to perform microbubble extraction. The extracted product was filtered using a 5-μm pore size filter (No. 2, HYUNDAI MICRO), dried for concentration, and dried in vacuo for use as a sample.

In addition, in this case, when generating the bubbles in the microbubble generator using air in the atmosphere, the following conditions were set: a pressure in a range of 3 to 4 bar and an air gas flow rate in a range of 3 to 4 L/min.

TABLE 1

| | Extraction method | Pressure | Gas flow rate | Extrac-tion solvent | Extrac-tion time | Extraction temper-ature |
|---|---|---|---|---|---|---|
| Example 1 | Extraction using microbubbles | 4 bar | 4 L/min | 50% (v/v) ethanol aqueous solution | 5 hours | 50° C. |
| Example 2 | Extraction using microbubbles | 4 bar | 3 L/min | 40% (v/v) ethanol aqueous solution | 3 hours | 60° C. |
| Example 3 | Extraction using microbubbles | 3 bar | 4 L/min | 60% (v/v) ethanol aqueous solution | 4 hours | 70° C. |

Comparative Examples 1 to 13. Preparation of Extract Under Comparison Conditions Extracts of *Cyperus rotundus* were prepared, but the extraction methods varied under different conditions as follows.

TABLE 2

| Extract | Extraction method | Pres-sure | Gas flow rate | Extraction solvent | Extrac-tion time | Extrac-tion temper-ature |
|---|---|---|---|---|---|---|
| Comparative Example 1 | Extraction using microbubbles | 4 bar | 4 L/min | 50% (v/v) ethanol aqueous solution | 7 hours | 50° C. |
| Comparative Example 2 | Extraction using microbubbles | 4 bar | 4 L/min | 50% (v/v) ethanol aqueous solution | 1 hour | 50° C. |
| Comparative Example 3 | Extraction using microbubbles | 4 bar | 4 L/min | 50% (v/v) ethanol aqueous solution | 5 hours | 30°° C. |
| Comparative Example 4 | Extraction using microbubbles | 2 bar | 4 L/min | 50% (v/v) ethanol aqueous solution | 5 hours | 50° C. |
| Comparative Example 5 | Extraction using microbubbles | 5 bar | 4 L/min | 50% (v/v) ethanol aqueous solution | 5 hours | 50° C. |
| Comparative Example 6 | Extraction using microbubbles | 4 bar | 2 L/min | 50% (v/v) ethanol aqueous solution | 5 hours | 50° C. |
| Comparative Example 7 | Extraction using microbubbles | 4 bar | 5 L/min | 50% (v/v) ethanol aqueous solution | 5 hours | 50° C. |
| Comparative Example 8 | Extraction using microbubbles | 4 bar | 4 L/min | water | 5 hours | 50° C. |
| Comparative Example 9 | Extraction using microbubbles | 4 bar | 4 L/min | 10% (v/v) ethanol aqueous solution | 5 hours | 50° C. |
| Comparative Example 10 | Extraction using microbubbles | 4 bar | 4 L/min | 80% (v/v) ethanol aqueous solution | 5 hours | 50° C. |
| Comparative Example 11 | Extraction using microbubbles | 4 bar | 4 L/min | 99% ethanol | 5 hours | 50° C. |
| Comparative Example 12 | Static extraction using solvent (not involving bubble treatment) | | | 50% (v/v) ethanol aqueous solution | 5 hours | 50° C. |
| Comparative Example 13 | Static extraction using solvent (not involving bubble treatment) | — | — | Water | 5 hours | 90° C. |

Experimental Example 1. Examination of Active Ingredient in Each Extract

A standard product of α-cyperone, a marker component in the extract, was purchased from Sigma-Aldrich. 10 mg of the standard product was dissolved in 100 ml of 99% methanol, and 50 mg of each sample was dissolved in 50 ml of 99% methanol.

Waters e2695/2998 UVD was used as an analysis system, and Capcell Pak C18 UG 120 (5 µm, 4.6×250 mm) was used as a column. As concentration gradient solvents for elution, 0.1% formic acid solution was used as solvent A, and ACN was used as solvent B. Elution was performed for 80 minutes in 13 steps such that the concentration ratio of solvent A to solvent B changed from 100:0 (v:v) to 0:100 (v:v).

The content of the finally obtained active ingredient in each sample is shown in Table 3 below.

TABLE 3

| Extract | α-cyperone (ppm) |
|---|---|
| Example 1 | 53241.41 |
| Example 2 | 51434.03 |
| Example 3 | 50463.39 |
| Comparative Example 1 | 40454.07 |
| Comparative Example 2 | 42523.03 |
| Comparative Example 3 | 34253.35 |
| Comparative Example 4 | 33423.09 |
| Comparative Example 5 | 34523.01 |
| Comparative Example 6 | 42234.23 |
| Comparative Example 7 | 40234.02 |
| Comparative Example 8 | 35523.42 |
| Comparative Example 9 | 35245.30 |
| Comparative Example 10 | 39283.43 |
| Comparative Example 11 | 34234.52 |
| Comparative Example 12 | 34526.35 |
| Comparative Example 13 | 35422.34 |

Through the results of Table 3, the extracts of Examples 1 to 3 of the present disclosure are confirmed to contain α-cyperone, the active compound, at the highest content.

Experimental Example 2. Cytotoxicity Examination of Sample

To examine the cytotoxicity of each extract prepared in Examples 1 to 3 and Comparative Examples 1 to 13, an MTT assay was performed. First, RAW 264.7 cells were dispensed in a 96-well plate at a cell concentration of $5\times10^4$ cells/well. Then, each sample dissolved in DMSO was added to set each concentration after 24 hours. After removing the medium when 24 hours elapsed, 40 µL of an MTT reagent (in PBS 2.5 mg/mL) was added to each well and reacted in an incubator for 4 hours, followed by removing the supernatant again. 100 µL of DMSO was dispensed in each well for complete dissolution. Absorbance was measured at a wavelength of 540 nm using a spectrophotometer.

TABLE 4

| | Cell viability of group treated with each extract compared to that of control group (%) | | |
|---|---|---|---|
| | 50 ppm | 100 ppm | 250 ppm |
| Example 1 | 99.28 | 97.16 | 106.48 |
| Example 2 | 99.93 | 98.36 | 103.05 |
| Example 3 | 98.85 | 99.63 | 99.52 |
| Comparative Example 1 | 97.64 | 98.52 | 98.30 |
| Comparative Example 2 | 98.33 | 99.40 | 99.64 |
| Comparative Example 3 | 101.42 | 98.34 | 98.21 |
| Comparative Example 4 | 99.05 | 99.65 | 103.92 |
| Comparative Example 5 | 98.52 | 99.06 | 106.04 |

TABLE 4-continued

| | Cell viability of group treated with each extract compared to that of control group (%) | | |
|---|---|---|---|
| | 50 ppm | 100 ppm | 250 ppm |
| Comparative Example 6 | 97.34 | 99.53 | 103.6 |
| Comparative Example 7 | 99.43 | 98.36 | 99.35 |
| Comparative Example 8 | 107.52 | 99.23 | 99.52 |
| Comparative Example 9 | 98.66 | 98.52 | 98.61 |
| Comparative Example 10 | 99.34 | 100.13 | 106.35 |
| Comparative Example 11 | 99.43 | 103.44 | 105.42 |
| Comparative Example 12 | 98.56 | 97.02 | 103.58 |
| Comparative Example 13 | 100.20 | 98.14 | 108.69 |

As a result, as shown in Table 4, assuming that the value of the control group was 100%, all the extracts were confirmed to exhibit a cell viability of 97.0% or higher under concentrations of up to 250 μg/ml, confirming that there was no cytotoxicity. Subsequent experiments were conducted at concentrations of 250 μg/ml or lower.

Experimental Example 3. Measurement of NO Production

To examine the inhibitory activity of each extract prepared in Examples 1 to 3 and Comparative Examples 1 to 13 on nitric oxide (NO) production, RAW 264.7 cell lines, mouse macrophage cells, were used for an experiment. RAW 264.7 cells were dispensed in a 96-well plate at a cell concentration of $1.0 \times 10^4$ cells/well, and incubated in an incubator supplied with 5% $CO_2$ at a temperature of 37° C. for 24 hours.

Next, the 96-well plate was each independently treated with serially diluted samples and stimulants. In this case, LPS, serving as the stimulant, was set to have a final concentration of 1 μg/mL. 100 μL of supernatant of the cells incubated for 24 hours was taken and put into a new 96-well plate. Then, Griess A and Griess B reagents were mixed in a ratio of 1:1, and 100 μL of the resulting mixture was added to each well. The reaction was performed at room temperature for 10 minutes to measure absorbance at a wavelength of 540 nm.

Nitric oxide production was calculated using the following equation.

NO production rate (%)=(Sample absorbance/Control absorbance)×100

The O.D value of the cells treated with 1 μg/mL of LPS was converted to 100% to show the measurement results, and this value was expressed as a control group.

TABLE 5

| | NO production rate of group treated with each extract compared to that of control group (treated with LPS alone) (%) | | |
|---|---|---|---|
| | 50 ppm + LPS | 100 ppm + LPS | 250 ppm + LPS |
| Example 1 | 76.95 | 47.14 | 5.04 |
| Example 2 | 79.27 | 49.62 | 7.53 |
| Example 3 | 77.35 | 51.22 | 9.23 |

TABLE 5-continued

| | NO production rate of group treated with each extract compared to that of control group (treated with LPS alone) (%) | | |
|---|---|---|---|
| | 50 ppm + LPS | 100 ppm + LPS | 250 ppm + LPS |
| Comparative Example 1 | 85.41 | 74.05 | 38.31 |
| Comparative Example 2 | 88.23 | 74.30 | 49.54 |
| Comparative Example 3 | 85.34 | 75.32 | 38.23 |
| Comparative Example 4 | 89.34 | 81.64 | 43.96 |
| Comparative Example 5 | 88.53 | 74.02 | 46.54 |
| Comparative Example 6 | 97.31 | 72.13 | 33.46 |
| Comparative Example 7 | 89.30 | 75.34 | 39.25 |
| Comparative Example 8 | 87.52 | 82.41 | 49.42 |
| Comparative Example 9 | 98.64 | 73.42 | 38.01 |
| Comparative Example 10 | 89.34 | 72.25 | 36.30 |
| Comparative Example 11 | 89.64 | 84.34 | 35.44 |
| Comparative Example 12 | 98.26 | 72.53 | 43.63 |
| Comparative Example 13 | 85.34 | 72.52 | 38.45 |

As a result, as shown in Table 5, the extracts of Examples 1 to 3 of the present disclosure were confirmed to exhibit inhibitory effects on the NO production in a concentration-dependent manner. However, the extracts that failed to meet this standard insignificantly inhibited NO production and thus were found to have low anti-inflammatory efficacy.

Experimental Example 4. Examination of Expression Level of Genes Related to Anti-Inflammation RAW 264.7 cells were dispensed in a 6-well plate at a cell concentration of $4.0 \times 10^5$ cells/well, and incubated in an incubator supplied with 5% $CO_2$ at a temperature of 37° C. for 24 hours. Each extract sample was set to have a final concentration of 100 ppm, and LPS serving as a stimulant was reacted for 4 hours to have a concentration of 1 μg/mL. After removing the supernatant from the medium, the resulting product was washed with PBS and dissolved in 500 μL of NucleoZOL (Macherey-Nagel, Germany). Then, 200 μL of sterile distilled water was added to perform centrifugation for 15 minutes, and 500 μL of the resulting supernatant was transferred to a new tube. Next, 500 μL of isopropanol was added to perform centrifugation for 10 minutes. After removing the supernatant, 75% (v/v) ethanol aqueous solution was added to perform centrifugation again for 5 minutes. The resulting product was dried at room temperature by removing the supernatant and then dissolved by dispensing 50 μL of diethyl pyrocarbonate-distilled water (DEPC-DW). As a result, RNA was quantified using a spectrophotometer.

Next, HiSenScript™ RH(−) RT PreMix Kit was used to add and mix 1 μg of the quantified RNA and DEPC-DW to have a total volume of 20 μL. CDNA synthesis was performed under the following conditions: a temperature of 42° C. for 30 minutes, a temperature of 85° C. for 10 minutes, and a temperature of 4° C. ∞. The complementary DNA (cDNA) synthesized was mixed by adding 10 μL of 2×

Real-Time PCR Master Mix (BioFACT), 1 μL of cDNA, 1 μL of a forward primer (10 pmole/μL), 1 μL of a reverse primer (10 pmole/μL), and DEPC-DW to have a total volume of 20 μL. As primers for the genes to be confirmed, components disclosed in Table 6 below were used.

TABLE 6

| Name | | Primer Sequence (5'→3') |
|------|------|------|
| TNF-α | Forward | GGTGCCTATGTCTCAGCCTCTT (SEQ ID NO: 1) |
| | Reverse | GCCATAGAACTGATGAGAGGGAG (SEQ ID NO: 2) |
| IL-1β | Forward | TGGACCTTCCAGGATGAGGACA (SEQ ID NO: 3) |
| | Reverse | GTTCATCTCGGAGCCTGTAGTG (SEQ ID NO: 4) |
| IL-6 | Forward | TACCACTTCACAAGTCGGAGGC (SEQ ID NO: 5) |
| | Reverse | CTGCAAGTGCATCATCGTTGTTC (SEQ ID NO: 6) |
| COX-2 | Forward | GCGACATACTCAAGCAGGAGCA (SEQ ID NO: 7) |
| | Reverse | AGTGGTAACCGCTCAGGTGTTG (SEQ ID NO: 8) |
| GAPDH | Forward | CATCACTGCCACCCAGAAGACTG (SEQ ID NO: 9) |
| | Reverse | ATGCCAGTGAGCTTCCCGTTCAG (SEQ ID NO: 10) |

Thereafter, PCR was performed using real-time polymerase chain reaction (Real-Time PCR) equipment at 50 cycles under the following conditions: a temperature of 95° C. for 15 minutes, a temperature of 95° C. for 20 seconds, and a temperature of 60° C. for 40 seconds. Then, relative quantitative analysis (ΔCt value) was performed on the experimental results to analyze the mRNA expression of each factor.

The analysis result values of expression level for each gene are shown in Table 7 below.

TABLE 7

| | Relative mRNA expression (% of control) | | | |
|------|------|------|------|------|
| | IL-6 | COX-2 | IL-1β | TNF-α |
| Example 1 | 16.23 | 29.29 | 3.76 | 30.14 |
| Example 2 | 18.32 | 28.30 | 8.53 | 34.25 |
| Example 3 | 19.03 | 29.23 | 9.23 | 32.32 |
| Comparative Example 1 | 58.45 | 53.34 | 43.63 | 73.12 |
| Comparative Example 2 | 54.46 | 45.52 | 51.46 | 62.41 |
| Comparative Example 3 | 46.33 | 53.52 | 45.31 | 85.30 |
| Comparative Example 4 | 53.35 | 60.04 | 43.63 | 63.05 |
| Comparative Example 5 | 74.23 | 43.04 | 55.04 | 75.02 |
| Comparative Example 6 | 50.54 | 46.50 | 42.51 | 62.30 |
| Comparative Example 7 | 64.34 | 30.34 | 33.33 | 63.16 |
| Comparative Example 8 | 50.22 | 53.13 | 45.37 | 75.21 |
| Comparative Example 9 | 64.22 | 31.52 | 41.57 | 73.60 |
| Comparative Example 10 | 53.55 | 62.12 | 55.46 | 86.33 |
| Comparative Example 11 | 66.44 | 75.40 | 42.46 | 73.46 |

TABLE 7-continued

| | Relative mRNA expression (% of control) | | | |
|------|------|------|------|------|
| | IL-6 | COX-2 | IL-1β | TNF-α |
| Comparative Example 12 | 54.24 | 62.04 | 33.63 | 74.05 |
| Comparative Example 13 | 55.10 | 63.12 | 31.45 | 66.24 |

As a result of the confirmation, as shown in Table 7, the gene expression of each of the inflammatory expression factors, interleukin 6 (IL-6), cyclooxygenase-2 (COX-2), interleukin-1β (IL-1β), and tumor necrosis factor-α (TNF-α), was seen to be significantly inhibited in the case of the groups treated with the extract of Examples 1 to 3.

Experimental Example 5: Examination of Expression Level of Genes Related to Skin Barrier and Moisturizing Next, to examine a skin barrier strengthening effect, HaCaT cells were dispensed in a 6-well plate at a cell concentration of $2.0 \times 10^5$ cells/well, and incubated in an incubator supplied with 5% $CO_2$ at a temperature of 37° C. for 24 hours. PBS was used for washing so as to replace the medium with a DMEM medium free of FBS, and then each extract sample was set to have a final concentration of 100 ppm. RNA extraction and cDNA synthesis were performed under the same measurement conditions as in the examination of anti-inflammatory genes, and experiment on gene expression of aquaporin-3 (AQP-3), hyaluronan synthase 2 (HAS-2), claudin-1 (CLDN-1), cadherin 1 (CDH1), filaggrin (FLG), and involucrin (IVL) was performed in the same manner for examination. Primers used at this time are shown in Table 8 below. In addition, gene expression is shown in Table 9 below by setting the result value of the comparison group (untreated group) to 100%.

TABLE 8

| Name | | Primer Sequence (from 5'→3') |
|------|------|------|
| AQP-3 | Forward | CCGTGACCTTTGCCATGTGCTT (SEQ ID NO: 11) |
| | Reverse | TTGTCGGCGAAGTGCCAGATTG (SEQ ID NO: 12) |
| HAS-2 | Forward | CAGAAGATGACCTTTACATGATGGA (SEQ ID NO: 13) |
| | Reverse | GGACCCTTTTCGTGGAAGTTG (SEQ ID NO: 14) |
| CLDN-1 | Forward | CCGGCGACAACATCGTGAC (SEQ ID NO: 15) |
| | Reverse | CGGGTTGCTTGCAATGTGC (SEQ ID NO: 16) |
| CDH1 | Forward | TGAAGGTGACAGAGCCTCTGGAT (SEQ ID NO: 17) |
| | Reverse | TGGGTGAATTCGGGCTTGTT (SEQ ID NO: 18) |
| FLG | Forward | GCTGAAGGAACTTCTGGAAAAGG (SEQ ID NO: 19) |
| | Reverse | GTTGTGGTCTATATCCAAGTGATC (SEQ ID NO: 20) |
| IVL | Forward | AGCCTTACTGTGAGTCTGGTTG (SEQ ID NO: 21) |
| | Reverse | GGAGGAACAGTCTTGAGGAGC (SEQ ID NO: 22) |

TABLE 8-continued

| Name | | Primer Sequence (from 5'→3') |
|---|---|---|
| GAPDH | Forward | GTCTCCTCTGACTTCAACAGCG (SEQ ID NO: 23) |
| | Reverse | ACCACCCTGTTGCTGTAGCCAA (SEQ ID NO: 24) |

TABLE 9

| Extract | Relative mRNA expression (% of control) | | | | | |
|---|---|---|---|---|---|---|
| (100 ppm) | AQP-3 | HAS-2 | CLDN-1 | CDH1 | FLG | IVL |
| Example 1 | 234.3 | 167.31 | 234.9 | 245.3 | 193.2 | 162.3 |
| Example 2 | 219.2 | 157.3 | 223.3 | 235.0 | 191.4 | 152.2 |
| Example 3 | 225.0 | 156.2 | 223.5 | 233.6 | 184.3 | 154.3 |
| Comparative Example 1 | 143.2 | 125.3 | 166.2 | 165.1 | 146.2 | 123.8 |
| Comparative Example 2 | 142.5 | 132.6 | 152.0 | 152.4 | 133.4 | 132.5 |
| Comparative Example 3 | 134.5 | 112.6 | 160.8 | 155.6 | 145.3 | 112.5 |
| Comparative Example 4 | 143.4 | 134.2 | 142.5 | 162.0 | 122.6 | 125.6 |
| Comparative Example 5 | 146.3 | 140.4 | 153.6 | 172.5 | 143.3 | 113.7 |
| Comparative Example 6 | 142.6 | 134.3 | 125.3 | 166.6 | 136.2 | 120.5 |
| Comparative Example 7 | 124.6 | 123.3 | 112.6 | 153.3 | 130.3 | 114.6 |
| Comparative Example 8 | 139.2 | 129.5 | 156.2 | 136.0 | 133.6 | 122.3 |
| Comparative Example 9 | 132.0 | 131.2 | 140.3 | 154.5 | 146.5 | 115.4 |
| Comparative Example 10 | 125.3 | 122.0 | 152.8 | 140.3 | 123.0 | 123.5 |
| Comparative Example 11 | 149.3 | 115.5 | 133.6 | 135.4 | 114.8 | 110.6 |
| Comparative Example 12 | 125.5 | 125.2 | 154.4 | 122.2 | 113.9 | 113.3 |
| Comparative Example 13 | 129.3 | 129.2 | 121.0 | 121.3 | 115.2 | 116.4 |

According to what is shown in Table 9, as a result of analyzing the gene expression patterns of aquaporin-3 (AQP-3), hyaluronan synthase 2 (HAS-2), claudin-1 (CLDN-1), cadherin 1 (CDH1), filaggrin (FLG), and involucrin (IVL), which are related to the strengthening of the skin barrier, moisture, and moisturizing, the extracts of Examples 1 to 3 of the present disclosure are seen to enhance a skin moisturizing function and thus best suited for use as a cosmetic composition that strengthens the skin barrier.

Formulation Example 1 of Cosmetic Composition.
Preparation of Facial Water

Facial water was prepared using an existing method with the following contents: 5.0% by weight of the extract of Example 1, 5.2% by weight of propylene glycol, 1.5% by weight of oleyl alcohol, 3.2% by weight of ethanol, 3.2% by weight of polysorbate 20, 2.0% by weight of benzophenone-9, 1.0% by weight of a carboxyl vinyl polymer, 3.5% by weight of glycerin, traces of fragrance, traces of a preservative, and the remainder of purified water.

Formulation Example 2 of Cosmetic Composition.
Preparation of Lotion

A lotion was prepared using an existing method with the following contents: 5.0% by weight of the extract of Example 1, 1.0% by weight of cetostearyl alcohol, 0.8% by weight of glyceryl monostearate, 0.3% by weight of sorbitan monostearate, 1.0% by weight of polysorbate 60, 5.0% by weight of mineral oil, 3.0% by weight of cyclomethicone, 0.5% by weight of dimethicone, 0.1% by weight of allantoin, 5.0% by weight of glycerin, 2% by weight of alcohol, 3.0% by weight of propylene glycol, traces of fragrance, traces of a preservative, and the remainder of purified water.

Formulation Example 3 of Cosmetic Composition.
Preparation of Toner

A toner was prepared using an existing method with the following contents: 5.0% by weight of the extract of Example 1, 4.0% by weight of propylene glycol, 3.0% by weight of glycerin, 0.5% by weight of allantoin, 0.01% by weight of EDTA-2Na, 5.0% by weight of ethanol, 1.5% by weight of triethanolamine, 2.0% by weight of squalane, 2.5% by weight of beeswax, 1.0% by weight of polysorbate 60, 1.0% by weight of a carboxyl vinyl polymer, 2.5% by weight of sorbitan sesquioleate, traces of fragrance, traces of a preservative, and the remainder of purified water.

Formulation Example 4 of Cosmetic Composition.
Preparation of Cream

A cream was prepared using an existing method with the following contents: 5.0% by weight of the extract of Example 1, 0.7% by weight of polyoxyethylene sorbitan monostearate, 0.5% by weight of sorbitan sesquioleate, 0.6% by weight of cetyl alcohol, 0.75% by weight of stearic acid, 0.6% by weight of glyceryl monostearate, 15.0% by weight of liquid paraffin, 10.0% by weight of a carboxy vinyl polymer, 0.2% by weight of triethanolamine, traces of fragrance, traces of a preservative, and the remainder of purified water.

Experimental Example 6: Confirmation of Skin
Irritation Relief Effect

A human patch test was performed using the toner prepared in Formulation Example 3 of the cosmetic composition to evaluate skin irritation relief effect.

To this end, evaluation was performed on 20 adult female test subjects aged 20 to 55 years old (−1 day, test start date) using a spectrophotometer by washing a test site and then relaxing the skin for 30 minutes.

In this case, a chamber impregnated with a 1.0% aqueous solution of sodium lauryl sulfate (SLS) was attached to the test site for 24 hours to cause skin erythema. The attached chamber was removed from the test site, and the condition of the test site was examined (before product use, day 0).

An explanation of how to use the toner was given to the test subjects whose condition was measured after inducing erythema as described above, followed by applying a test product. Next, safety assessments and device evaluations were performed on the test subjects 24 hours, 48 hours, and 72 hours after product use to assess the efficacy. As a result, *a value was measured using a spectrophotometer, confirming that the *a value significantly decreased 72 hours after the product use.

TABLE 10

| | | *a value: measurement value | | | |
|---|---|---|---|---|---|
| Formulation of cosmetic product | Start date (−1 day) | Before product use (day 0) | 24 hours after product use | 48 hours after product use | 72 hours after product use |
| Toner of Formulation Example 3 containing extract of Example 1 | 6.993 | 8.837 | 9.985 | 9.036 | 8.309 |
| Toner free of extract | 6.996 | 8.688 | 10.543 | 9.679 | 9.064 |

As shown in Table 10, as a result of the test, even though the area where SLS was put alone showed redness of the skin at a maximum level after 24 hours, the skin condition was quickly recovered when applying the product containing the extract obtained in Example 1. However, in the case of a toner free of the extract, redness remained even after 72 hours.

Experimental Example 7: Expert Visual Assessment

The cream of Formulation Example 4 (containing 5% by weight of the extract of *Cyperus rotundus* prepared in Example 1) was compared with a cream containing the same contents other than the extract to test efficacy in clinical symptoms. This test was in performed by observing the same subjects until user assessment.

To this end, an appropriate amount of each cream was applied twice a day, morning and evening, on an area within 5 cm of the lower popliteal fossa of the subject who complained of pruritus, after cleansing, for a test period of 8 weeks. A total of 32 subjects were tested.

First, experts (dermatologists/specialists) visually assessed the level of erythema, scaling, induration, and fissuring according to the usage of the cream by the ESIF scale (erythema, scaling, induration, and fissuring) in Table 11 below.

TABLE 11

| | Erythema | Scaling | Induration | Fissure |
|---|---|---|---|---|
| 0 point | No sign | No sign | No sign | No sign |
| 1 point | Light to pink | Fine scaling | Lesions somewhat protruding compared to normal (protuberance with a size of about 0.5-mm) | Several superficial fissures |
| 2 point | Red but not dark red | Diffuse and thick scaling | Prominent indentation (protuberance with a size of about 0.75-mm protuberance) | Multiple fissures with medium depth |
| 3 point | Deep/dark red to purple | Excessively thick scaling, covering all lesions | Protuberances with a size of at least 1 mm | numerous and deep fissures |

In this case, while adding four variables to give each subject a total score ranging from 0 to 12 points by expert assessment, a person whose score exceeds 6 points may be considered to be in need of dermatological treatment and thus excluded from the test.

As a result of the examination, during the total period of 8 weeks, there were zero people whose results of summing the variables of erythema, scaling, induration, and fissures exceeded 6 points among all 32 subjects. In addition, no one was found to be unsuitable for the test or to have side effects, so the test was continued. Relevant results were not separately attached.

Experimental Example 8: Confirmation of Pruritus Improvement

The pruritus assessment performed on the subjects who had undergone the test for 8 weeks was assessed using a visual analogue scale (VAS). The test subject directly made a mark on a 10-cm segment, followed by measuring the length thereof. The rate of change in the pruritus scale was shown using the following equation. *Before product use: 0 weeks $$\text{Rate of change in pruritus scale (\%)} = \{(\text{pruritus scale after product use} - \text{pruritus scale before product use})/\text{pruritus scale before product use}\} \times 100$$

Figure 1:
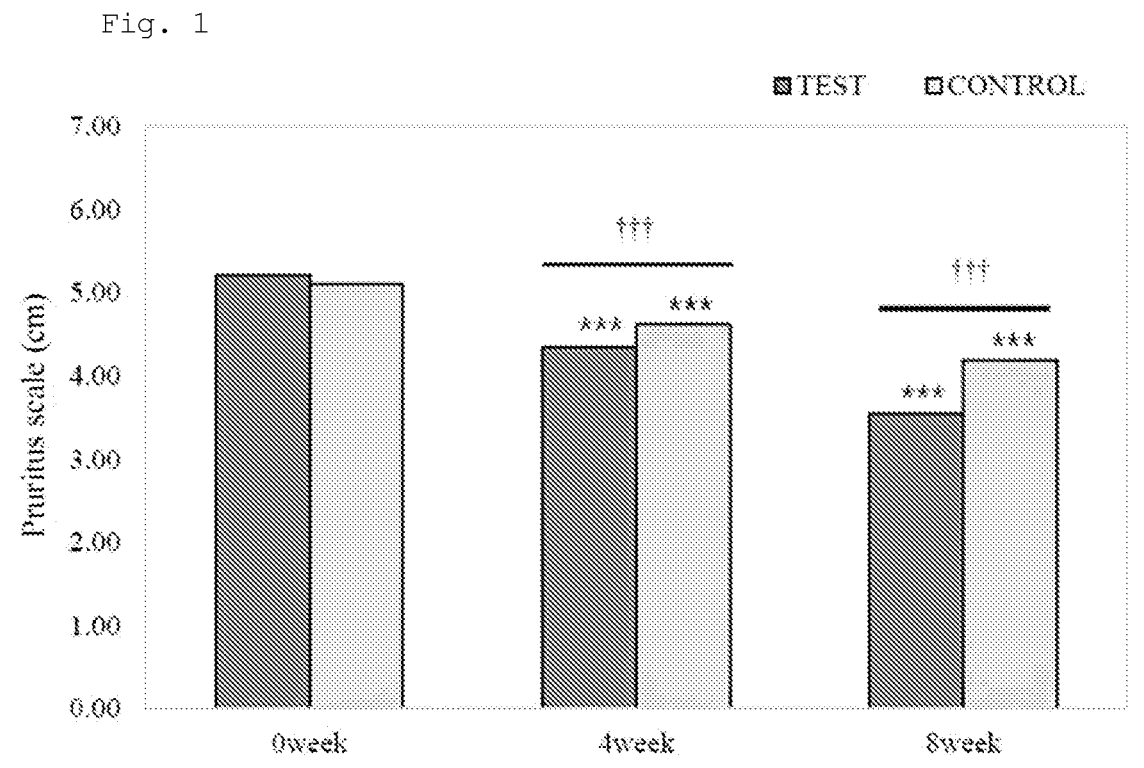

The results of the equation are shown in FIG. 1.

Referring to FIG. 1, the TEST cream containing the extract of *Cyperus rotundus* is confirmed to exhibit a significant pruritus relief effect after 4 weeks and 8 weeks, compared to the CONTROL cream, which is the group untreated with the extract.

Experimental Example 9: Confirmation of Transepidermal Water Loss and Skin Moisture Content Transepidermal water loss (TEWL) according to the usage of the cream was tested in accordance with the human body application test guideline [Guidance on Civil Petition] for cosmetics that help improve pruritus and the like by restoring skin barrier functions. Vapometer (Delfin, Finland) was used as a measurement device when measuring the transepidermal water loss. The lower the transepidermal water loss (TEWL), the lower the measured value. The measurement unit was $g/m^2/h$, and the results are shown in FIG. 2 using the following equation. *Before product use: 0 weeks $$\text{Rate of change in skin moisture content (\%)} = \{(\text{measured value after product use} - \text{measured value before product use})/\text{measured value before product use}\} \times 100$$

Figure 2:
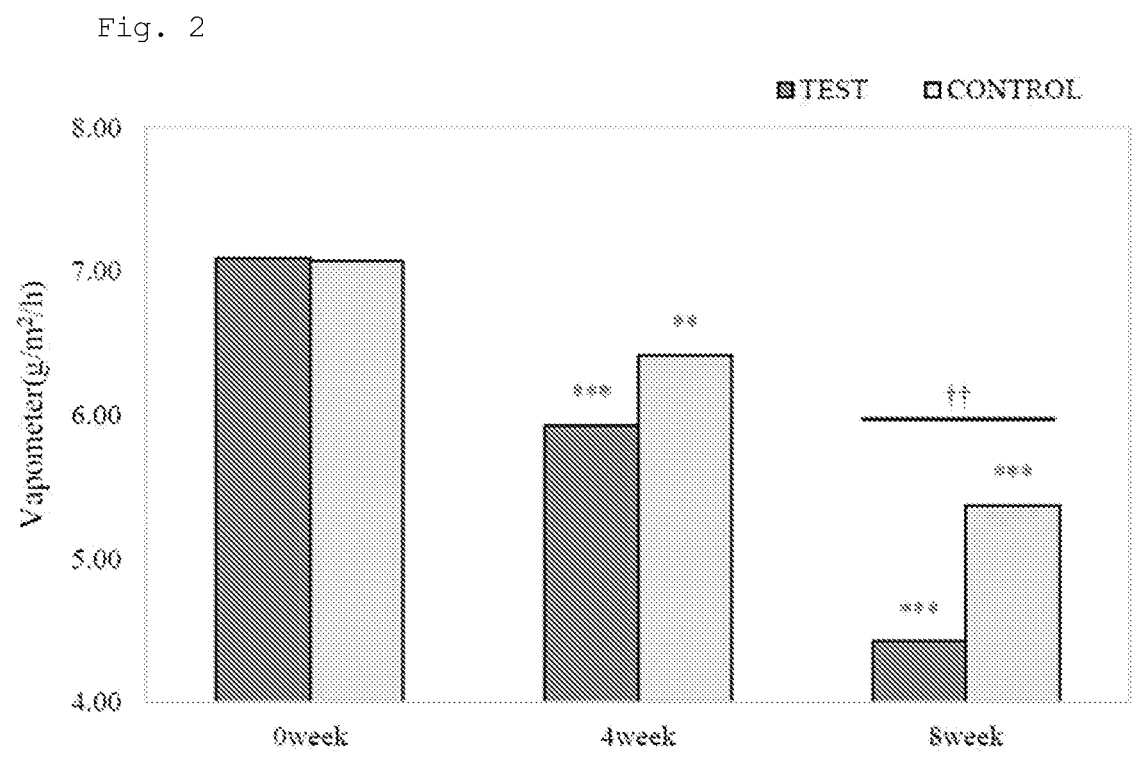

Referring to FIG. 2, the TEST cream containing the extract of *Cyperus rotundus* exhibited a significantly reduced transepidermal water loss, compared to the CONTROL cream, which is the group untreated with the extract.

Experimental Example 10: Confirmation of Skin Moisture Content

Measurement of skin moisture content according to the usage of the cream was performed using Corneometer CM825 (Courage-Khazaka Electronic GmbH, Germany). Using the corneometer, measurement of the capacitance of the current transmitted through a probe in contact with the skin is performed. The moisture content and the capacitance tend to be proportional to each other. Thus, the higher the moisture content, the higher the measured value. In addition, the measurement coefficient is arbitrary Unit (AU). Each result was converted using the following equation and shown in FIG. 3. *Before product use: 0 weeks.

$$\text{Rate of change in skin moisture content (\%)} = \{(\text{measured value after product use} - \text{measured value before product use})/\text{measured value before product use}\} \times 100$$

Referring to FIG. 3, the skin moisture content is also significantly increased in the group where the cream containing the extract of *Cyperus rotundus* of the present disclosure was put on the test subjects.

Experimental Example 11: Satisfaction of Test Subjects

The user satisfaction with the product according to criteria illustrated in Table 12 below was measured 4 weeks after the use of the cream containing the extract of *Cyperus rotundus* of the present disclosure and the cream of the control group, and then shown in Table 13.

TABLE 12

| Score | Criteria for formulation | Criteria for pruritus improvement |
|---|---|---|
| 1 | Extremely low | Significantly aggravated pruritus overall |
| 2 | Low | Aggravated pruritus overall |
| 3 | Moderate | No difference from before application |

18

TABLE 12-continued

| Score | Criteria for formulation | Criteria for pruritus improvement |
|---|---|---|
| 4 | High | Improved pruritus overall |
| 5 | Extremely high | Significantly improved pruritus overall |

TABLE 13

| | Fragrance | Absorbance | Elasticity | Lightness | Tone-up effect | Pruritus improvement |
|---|---|---|---|---|---|---|
| Cream of Formulation Example 4 (containing extract of *Cyperus rotundus* in Example 1) | 4.2 | 4.0 | 4.6 | 4.2 | 4.3 | 4.6 |
| Cream of control group (free of containing extract) | 3.2 | 3.1 | 3.0 | 2.9 | 3.3 | 3.2 |

As confirmed by the results of Table 13, the cream containing the extract of the present disclosure exhibited an excellent pruritus improvement effect. In addition, the formulation of the cream itself was highly preferable.

Through this result, the usefulness of the cream containing the extract of *Cyperus rotundus* of the present disclosure was able to be confirmed.

The invention claimed is:

1. A method of providing anti-inflammatory and skin-soothing effects to a subject in need thereof, comprising:

preparing a composition containing an extract of *Cyperus rotundus* extracted using warm microbubbles, and applying the composition to skin of the subject.

2. The method of claim 1, wherein the composition contains α-cyperone.

3. The method of claim 1, wherein the extract inhibits nitric oxide (NO) production.

4. The method of claim 1, wherein the extract inhibits expression of a gene selected from the group consisting of inflammatory expression factors interleukin 6 (IL-6), cyclooxygenase-2 (COX-2), interleukin-1β (IL-1β), and tumor necrosis factor-α (TNF-α).

5. The method of claim 1, wherein the extract has an efficacy of enhancing a skin barrier.

6. The method of claim 1, wherein the extract enhances expression of a gene selected from the group consisting of aquaporin-3 (AQP-3), hyaluronan synthase 2 (HAS-2), claudin-1 (CLDN-1), cadherin 1 (CDH1), filaggrin (FLG), and involucrin (IVL).

7. The method of claim 1, wherein the extract has an efficacy of relieving skin irritation.

8. The method of claim 1, wherein the subject suffers from erythema or pruritus.

* * * * *

SEQUENCE LISTING

```
Sequence total quantity: 24
SEQ ID NO: 1              moltype = DNA  length = 22
FEATURE                   Location/Qualifiers
source                    1..22
                          mol_type = other DNA
                          organism = synthetic construct
SEQUENCE: 1
ggtgcctatg tctcagcctc tt                                          22

SEQ ID NO: 2              moltype = DNA  length = 23
FEATURE                   Location/Qualifiers
source                    1..23
                          mol_type = other DNA
                          organism = synthetic construct
SEQUENCE: 2
gccatagaac tgatgagagg gag                                         23

SEQ ID NO: 3              moltype = DNA  length = 22
FEATURE                   Location/Qualifiers
source                    1..22
                          mol_type = other DNA
                          organism = synthetic construct
SEQUENCE: 3
tggaccttcc aggatgagga ca                                          22

SEQ ID NO: 4              moltype = DNA  length = 22
FEATURE                   Location/Qualifiers
source                    1..22
                          mol_type = other DNA
                          organism = synthetic construct
SEQUENCE: 4
gttcatctcg gagcctgtag tg                                          22

SEQ ID NO: 5              moltype = DNA  length = 22
FEATURE                   Location/Qualifiers
source                    1..22
                          mol_type = other DNA
```

-continued

```
                          organism = synthetic construct
SEQUENCE: 5
taccacttca caagtcggag gc                                                    22

SEQ ID NO: 6              moltype = DNA   length = 23
FEATURE                   Location/Qualifiers
source                    1..23
                          mol_type = other DNA
                          organism = synthetic construct
SEQUENCE: 6
ctgcaagtgc atcatcgttg ttc                                                   23

SEQ ID NO: 7              moltype = DNA   length = 22
FEATURE                   Location/Qualifiers
source                    1..22
                          mol_type = other DNA
                          organism = synthetic construct
SEQUENCE: 7
gcgacatact caagcaggag ca                                                    22

SEQ ID NO: 8              moltype = DNA   length = 22
FEATURE                   Location/Qualifiers
source                    1..22
                          mol_type = other DNA
                          organism = synthetic construct
SEQUENCE: 8
agtggtaacc gctcaggtgt tg                                                    22

SEQ ID NO: 9              moltype = DNA   length = 23
FEATURE                   Location/Qualifiers
source                    1..23
                          mol_type = other DNA
                          organism = synthetic construct
SEQUENCE: 9
catcactgcc acccagaaga ctg                                                   23

SEQ ID NO: 10             moltype = DNA   length = 23
FEATURE                   Location/Qualifiers
source                    1..23
                          mol_type = other DNA
                          organism = synthetic construct
SEQUENCE: 10
atgccagtga gcttcccgtt cag                                                   23

SEQ ID NO: 11             moltype = DNA   length = 22
FEATURE                   Location/Qualifiers
source                    1..22
                          mol_type = other DNA
                          organism = synthetic construct
SEQUENCE: 11
ccgtgacctt tgccatgtgc tt                                                    22

SEQ ID NO: 12             moltype = DNA   length = 22
FEATURE                   Location/Qualifiers
source                    1..22
                          mol_type = other DNA
                          organism = synthetic construct
SEQUENCE: 12
ttgtcggcga agtgccagat tg                                                    22

SEQ ID NO: 13             moltype = DNA   length = 25
FEATURE                   Location/Qualifiers
source                    1..25
                          mol_type = other DNA
                          organism = synthetic construct
SEQUENCE: 13
cagaagatga cctttacatg atgga                                                 25

SEQ ID NO: 14             moltype = DNA   length = 21
FEATURE                   Location/Qualifiers
source                    1..21
                          mol_type = other DNA
                          organism = synthetic construct
SEQUENCE: 14
ggaccctttt cgtggaagtt g                                                     21

SEQ ID NO: 15             moltype = DNA   length = 19
FEATURE                   Location/Qualifiers
source                    1..19
```

```
                              mol_type = other DNA
                              organism = synthetic construct
SEQUENCE: 15
ccggcgacaa catcgtgac                                                    19

SEQ ID NO: 16        moltype = DNA   length = 19
FEATURE              Location/Qualifiers
source               1..19
                     mol_type = other DNA
                     organism = synthetic construct
SEQUENCE: 16
cgggttgctt gcaatgtgc                                                    19

SEQ ID NO: 17        moltype = DNA   length = 23
FEATURE              Location/Qualifiers
source               1..23
                     mol_type = other DNA
                     organism = synthetic construct
SEQUENCE: 17
tgaaggtgac agagcctctg gat                                               23

SEQ ID NO: 18        moltype = DNA   length = 20
FEATURE              Location/Qualifiers
source               1..20
                     mol_type = other DNA
                     organism = synthetic construct
SEQUENCE: 18
tgggtgaatt cgggcttgtt                                                   20

SEQ ID NO: 19        moltype = DNA   length = 23
FEATURE              Location/Qualifiers
source               1..23
                     mol_type = other DNA
                     organism = synthetic construct
SEQUENCE: 19
gctgaaggaa cttctggaaa agg                                               23

SEQ ID NO: 20        moltype = DNA   length = 24
FEATURE              Location/Qualifiers
source               1..24
                     mol_type = other DNA
                     organism = synthetic construct
SEQUENCE: 20
gttgtggtct atatccaagt gatc                                              24

SEQ ID NO: 21        moltype = DNA   length = 22
FEATURE              Location/Qualifiers
source               1..22
                     mol_type = other DNA
                     organism = synthetic construct
SEQUENCE: 21
agccttactg tgagtctggt tg                                                22

SEQ ID NO: 22        moltype = DNA   length = 21
FEATURE              Location/Qualifiers
source               1..21
                     mol_type = other DNA
                     organism = synthetic construct
SEQUENCE: 22
ggaggaacag tcttgaggag c                                                 21

SEQ ID NO: 23        moltype = DNA   length = 22
FEATURE              Location/Qualifiers
source               1..22
                     mol_type = other DNA
                     organism = synthetic construct
SEQUENCE: 23
gtctcctctg acttcaacag cg                                                22

SEQ ID NO: 24        moltype = DNA   length = 22
FEATURE              Location/Qualifiers
source               1..22
                     mol_type = other DNA
                     organism = synthetic construct
SEQUENCE: 24
accaccctgt tgctgtagcc aa                                                22
```